(12) United States Patent
Ries et al.

(10) Patent No.: US 6,799,072 B2
(45) Date of Patent: Sep. 28, 2004

(54) ELECTRICALLY INSULATED COMPONENT SUB-ASSEMBLIES OF IMPLANTABLE MEDICAL DEVICES

(75) Inventors: Andrew J. Ries, Lino Lakes, MN (US); Mark D. Breyen, Plymouth, MN (US); John D. Norton, New Brighton, MN (US); Thomas P. Miltich, Maple Grove, MN (US); Steven J. May, Minnetonka, MN (US); Angela Rodgers, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 348 days.

(21) Appl. No.: 10/132,781

(22) Filed: Apr. 25, 2002

(65) Prior Publication Data

US 2003/0204216 A1 Oct. 30, 2003

(51) Int. Cl.$^7$ .............................................. A61N 1/372
(52) U.S. Cl. ...................................................... 607/36
(58) Field of Search ............................... 607/5, 6, 7, 8, 607/36, 37, 38; 361/522, 523, 524, 525

(56) References Cited

U.S. PATENT DOCUMENTS

| | | | |
|---|---|---|---|
| 4,254,775 A | 3/1981 | Langer | 128/419 D |
| 4,314,562 A | 2/1982 | Ware | |
| 4,942,501 A | 7/1990 | MacFarlane et al. | 361/523 |
| 5,086,374 A | 2/1992 | MacFarlane et al. | 361/525 |
| 5,131,388 A | 7/1992 | Pless et al. | 128/419 D |
| 5,146,391 A | 9/1992 | MacFarlane et al. | 361/525 |
| 5,153,820 A | 10/1992 | MacFarlane et al. | 361/525 |
| 5,370,669 A | 12/1994 | Daglow et al. | 607/36 |
| 5,522,851 A | 6/1996 | Fayram | 607/5 |
| 5,562,801 A | 10/1996 | Nulty | 156/643.1 |
| 5,628,801 A | 5/1997 | MacFarlane et al. | 29/25.03 |
| 5,741,313 A | 4/1998 | Davis et al. | 607/36 |
| 5,748,439 A | 5/1998 | MacFarlane et al. | 361/525 |
| 5,749,910 A | 5/1998 | Brumwell et al. | 607/36 |
| 5,814,090 A | 9/1998 | Latterell et al. | 607/36 |
| 6,026,325 A | 2/2000 | Weinberg et al. | 607/36 |

FOREIGN PATENT DOCUMENTS

WO    WO 02/02185 A2    1/2002    .......... A61N/1/372

OTHER PUBLICATIONS

Troup, "Implantable Cardioverters and Defibrillators", Current Problems in Cardiology, vol. XIV, No. 12, Dec. 1989, Year Book Publishers, Chicago.
Lunsmann et al., "High Energy Density Capacitors for Implantable Defibrillators", CARTS 96: 16$^{th}$ Capacitor and Resistor Technology Symposium Mar. 11–15, 1996, pp. 35–39.
"Thermoforming", Encyclopedia of Polymer Science and Engineering, vol. 16, 2$^{nd}$ edition, published by John Wiley & Sons, pp. 807–832, 1989.

Primary Examiner—George Manuel
(74) Attorney, Agent, or Firm—Michael C. Soldner; Girma Wolde-Michael

(57) ABSTRACT

Implantable medical devices (IMDs) and their various components, particularly methods and apparatus for electrically isolating and supporting components of an IMD IPG, e.g., capacitors of a capacitor sub-assembly, thereof in volumetrically efficient ways. A capacitor sub-assembly comprising two or more capacitors stacked side-by-side such that the facing capacitor case major sides are separated by a reliable and simple to apply insulation layer of minimal thickness is disclosed for assembly with other components of an ICD IPG into an IPG housing. A shape conforming insulating spacer is formed of an insulating polymer to conform to the shape of a first capacitor case major side and the perimeter of that major side. The shape conforming insulating spacer is simply applied or adhered by adhesive layers, bands or patterns to one or both of the facing capacitor case major sides.

43 Claims, 8 Drawing Sheets

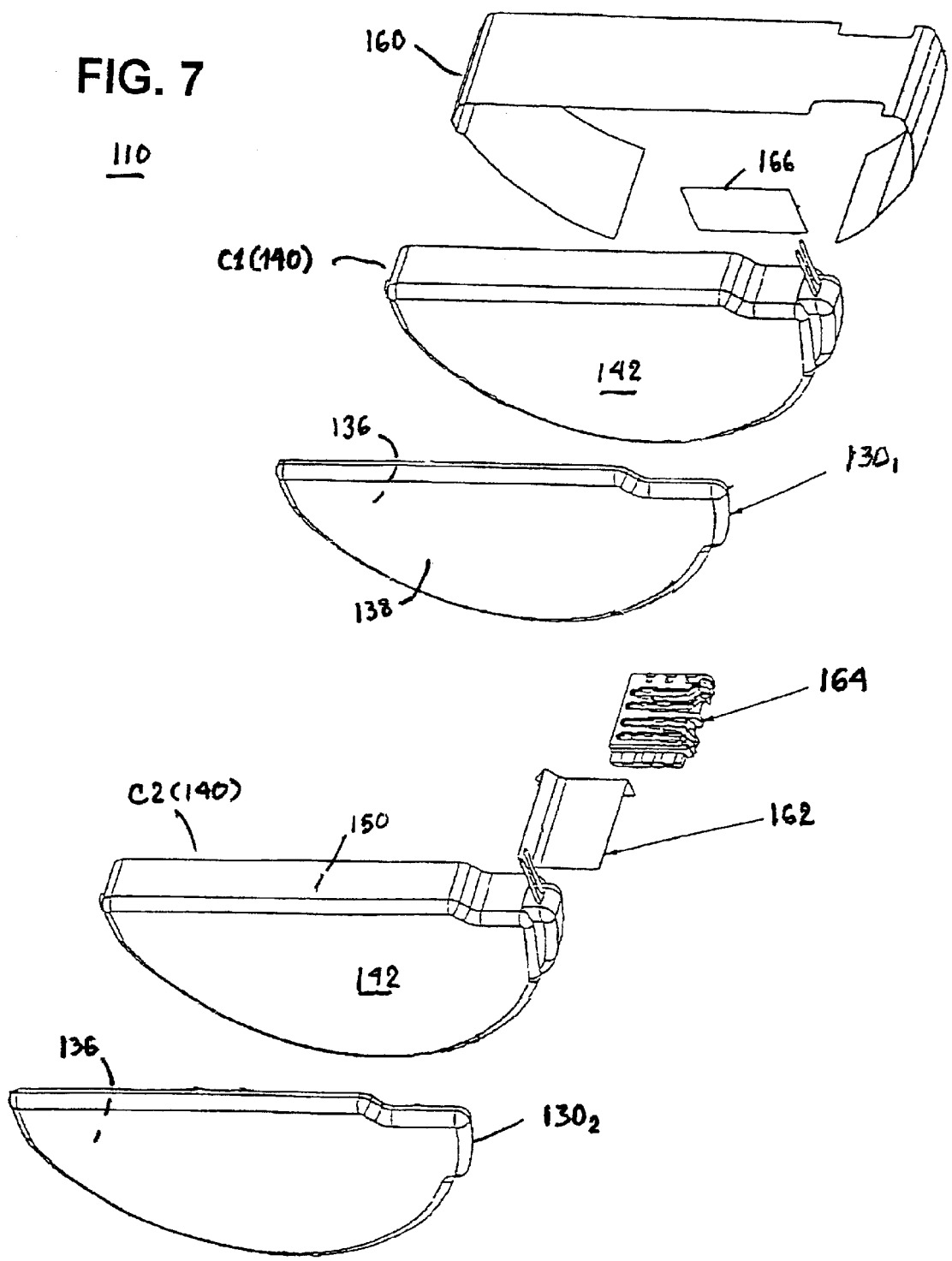

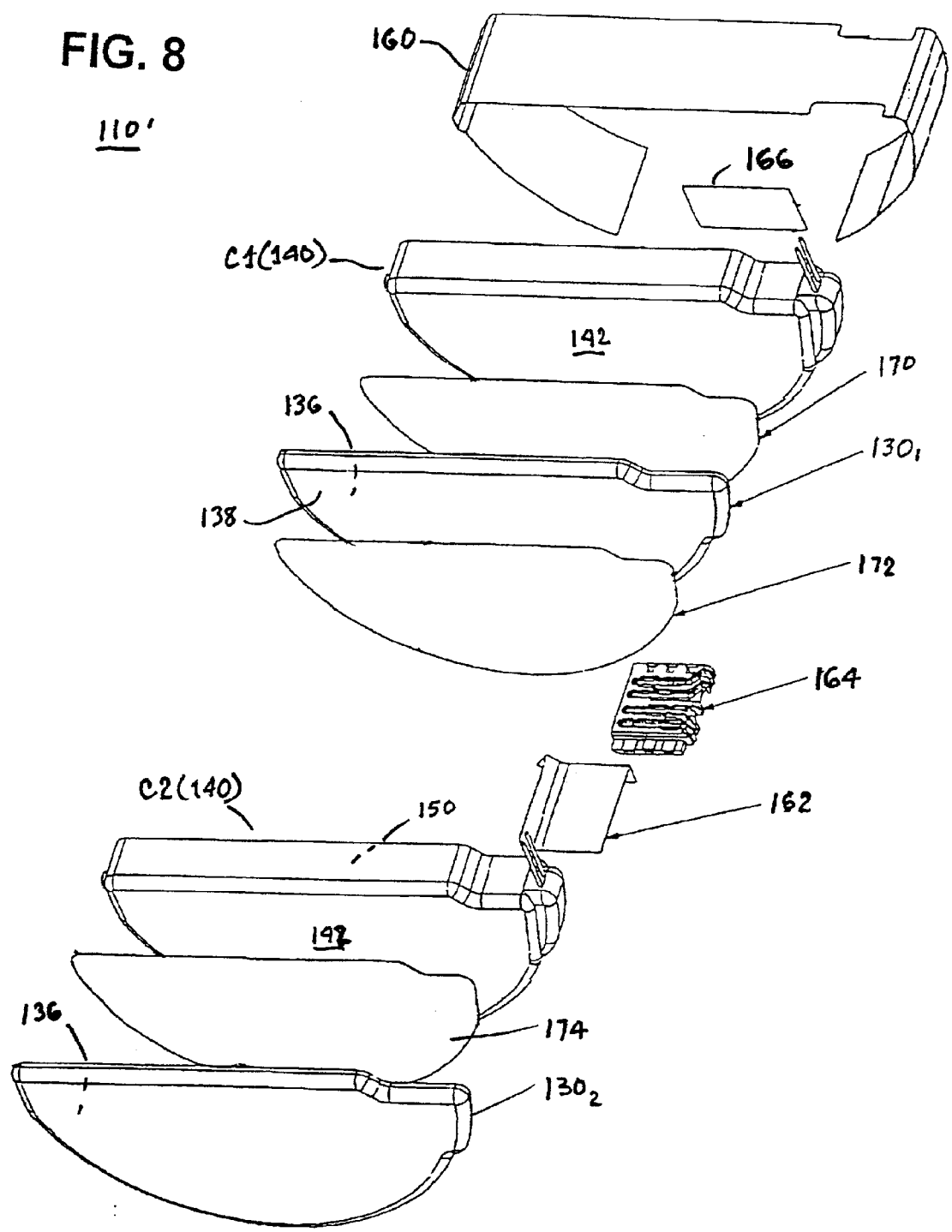

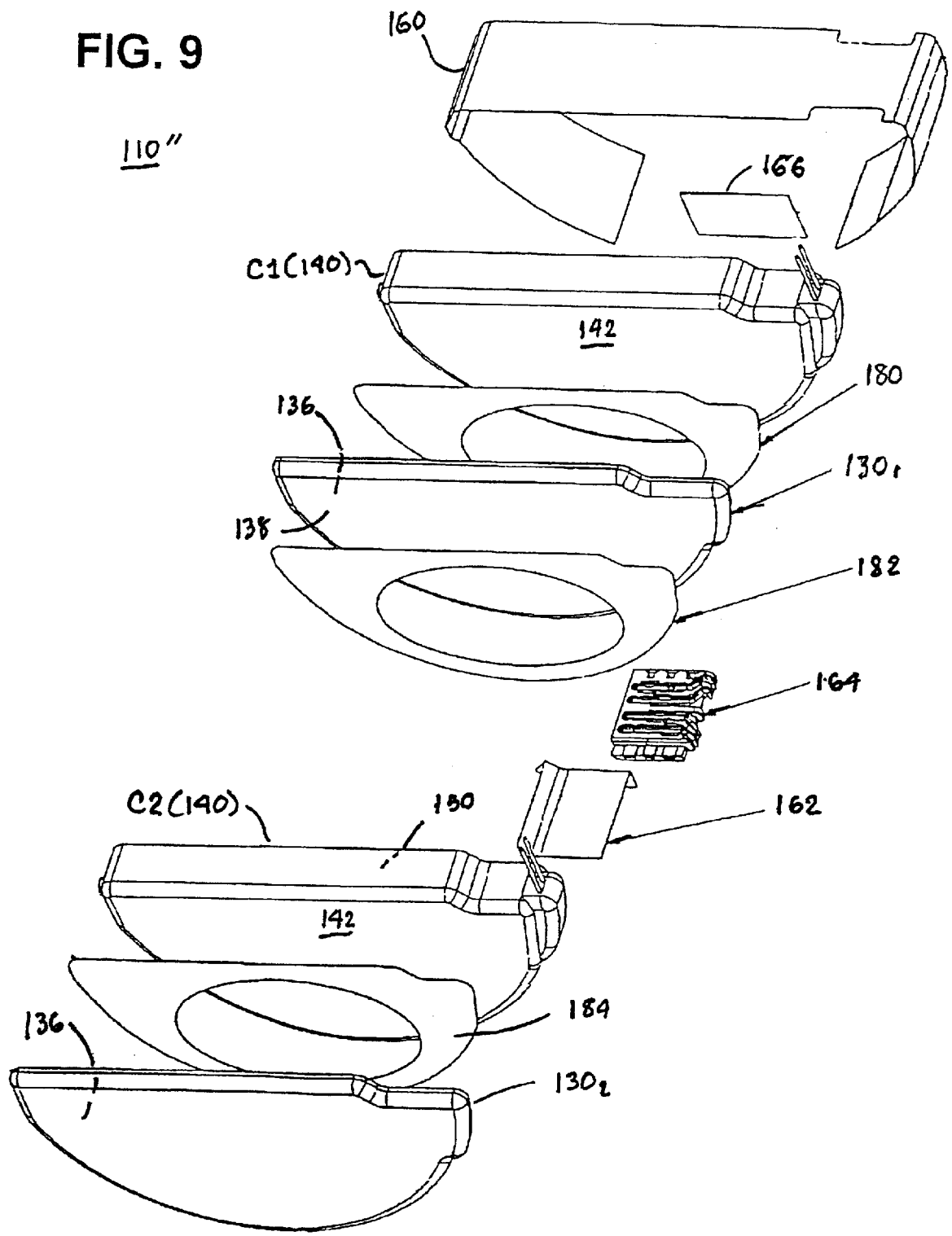

ELECTRICALLY INSULATED COMPONENT SUB-ASSEMBLIES OF IMPLANTABLE MEDICAL DEVICES

FIELD OF THE INVENTION

This invention relates to implantable medical devices (IMDs), particularly methods and apparatus for electrically isolating and supporting component sub-assemblies formed of multiple components in volumetrically efficient ways.

BACKGROUND OF THE INVENTION

A wide variety of IMDs are known in the art. Of particular interest are implantable cardioverter-defibrillators (ICDs) that deliver relatively high-energy cardioversion and/or defibrillation shocks to a patient's heart when a malignant tachyarrhythmia, e.g., atrial or ventricular fibrillation, is detected. The shocks are developed by discharge of one or more high voltage electrolytic capacitor that is charged up from an ICD battery. Current ICDs typically possess single or dual chamber pacing capabilities for treating specified chronic or episodic atrial and/or ventricular bradycardia and tachycardia and were referred to previously as pacemaker/cardioverter/defibrillators (PCDs). Earlier developed automatic implantable defibrillators (AIDs) did not have cardioversion or pacing capabilities. For purposes of the present invention ICDs are understood to encompass all such IMDs having at least high voltage cardioversion and/or defibrillation capabilities.

Energy, volume, thickness and mass are critical features in the design of ICD implantable pulse generators (IPGs) that are coupled to the ICD leads to form the completed ICD. The battery(s) and high voltage capacitor(s) used to provide and accumulate the energy required for the cardioversion/defibrillation shocks have historically been relatively bulky and expensive. Presently, ICD IPGs typically have a volume of about 40 to about 60 cc, a thickness of about 13 mm to about 16 mm and a mass of approximately 100 grams.

It is desirable to reduce the volume, thickness and mass of such capacitors and ICD IPGs without reducing deliverable energy. Doing so is beneficial to patient comfort and minimizes complications due to erosion of tissue around the ICD IPG. The size of the ICD IPG is commonly measured in terms of its volume, i.e., displacement. The volume is determined largely by the size and arrangement of the major components enclosed within an IPG "can" or hermetically sealed housing and the size of a connector header mounted to the IPG housing for making electrical connection with ICD leads. The major components within the ICD IPG housing include one or more battery, one or more high voltage capacitor, electronic modules, a telemetry antenna, a large internal discharge resistor (in early ICD IPGs), and any plastic frame or skeleton, spaces or liners supporting these components within the can. Also, the volume of the interconnection wiring between these components can be appreciable.

The high voltage capacitor(s) are among the largest volume components that must be enclosed within the ICD IPG housing. Thus, a great deal of effort has been expended in decreasing the volume of the capacitor(s) to allow for the balanced addition of volume to the battery, thereby increasing longevity of the ICD IPG, or balanced addition of new components, thereby adding functionality to the ICD IPG or to decrease the volume of the ICD IPG housing.

Various types of flat and spiral-wound capacitors are known in the art, some examples of which are described as follows and/or may be found in the patents listed in Table 1 of commonly assigned U.S. Pat. No. 6,006,133. Typically, an electrolytic capacitor is fabricated with a capacitor case enclosing a "valve metal" (e.g., aluminum) anode layer (or "electrode"), a valve metal (e.g. aluminum) cathode layer (or "electrode"), and a Kraft paper or fabric gauze spacer or separator impregnated with a solvent based liquid electrolyte interposed therebetween. The aluminum anode layer is typically fabricated from aluminium foil that is first etched and then "formed" by passage of electrical current through the anode layer to oxidize the etched surfaces so that the aluminium oxide functions as a dielectric layer. The electrolyte comprises an ion producing salt that is dissolved in a solvent and provides ionic electrical conductivity between the cathode layer and the aluminum oxide dielectric layer. The energy of the capacitor is stored in the electromagnetic field generated by opposing electrical charges separated by the aluminum oxide layer disposed on the surface of the anode layer and is proportional to the surface area of the etched aluminum anode layer. Thus, to minimize the overall volume of the capacitor one must maximize anode surface area per unit volume without increasing the capacitor's overall (i.e., external) dimensions. The separator material, anode and cathode layer terminals, internal packaging, electrical interconnections, and alignment features and cathode material further increase the thickness and volume of a capacitor. Consequently, these and other components in a capacitor and the desired capacitance limit the extent to which its physical dimensions may be reduced.

Some ICD IPGs employ commercial photoflash capacitors similar to those described by Troup in "Implantable Cardioverters and Defibrillators," *Current Problems in Cardiology*, Volume XIV, Number 12, December 1989, Year Book Medical Publishers, Chicago, and as described in U.S. Pat. No. 4,254,775. The electrodes or anode and cathodes are wound into anode and cathode layers separated by separator layers of the spiral. Most commercial photoflash capacitors contain a core of separator paper intended to prevent brittle, highly etched aluminum anode foils from fracturing during winding of the anode, cathode, and separator layers into a coiled configuration. The cylindrical shape and paper core of commercial photoflash capacitors limits the volumetric packaging efficiency and thickness of an ICD IPG housing made using same.

The early ICD IPG depicted in the '778 patent is much larger in volume and weight than current ICD IPGs due to use of such large cylindrical capacitors as well as large volume batteries, large discrete electrical components, circuit boards and the supporting skeleton for these components. The capacitors are supported and electrically isolated from one another and the batteries and the electrical circuitry by end cups and spacers and are cushioned from the housing itself by electrical insulating tape wound about the capacitors and batteries. An appreciable amount of unfilled space appears to remain in the ICD IPG housing. Moreover, tedious hand assembly appears to have been necessary to assemble these components. Nevertheless, similar component arrangements and assembly techniques have continued to be used until recently with more compact integrated circuit modules as evidenced by the ICD IPG depicted in U.S. Pat. Nos. 5,741,313, 5,749,910, 5,814,090, and 6,026,325, for example.

Recently developed ICD IPGs employ one or more flat or "prismatic", high voltage, electrolytic capacitor to overcome some of the packaging and volume disadvantages associated with cylindrical photoflash capacitors. Flat aluminum electrolytic capacitors for use in ICD IPGs have been disclosed, e.g., those improvements described in "High Energy Density Capacitors for Implantable Defibrillators" presented by P. Lunsmann and D. MacFarlane at *CARTS 96: 16th Capacitor and Resistor Technology Symposium,* 11–15 March 1996, and at *CARTS-EUROPE 96: 10th European Passive Components Symposium.,* 7–11 October 1996, pp. 35–39. Further features of flat electrolytic capacitors for use in ICD IPGs are disclosed in the above-referenced '133 patent and in U.S. Pat. Nos. 4,942,501; 5,086,374; 5,131,388; 5,146,391; 5,153,820; 5,522,851, 5,562,801; 5,628,801; and 5,748,439, all issued to MacFarlane et al. For example, U.S. Pat. Nos. 5,131,388 and 5,522,851 disclose a flat aluminium electrolytic capacitor having a plurality of stacked capacitor layers each comprising an "electrode stack sub-assembly". Each capacitor layer contains one or more anode sheet forming an anode layer having an anode tab, a cathode sheet or layer having a cathode tab and a separator for separating the anode layer from the cathode layer. The electrode stack sub-assembly is fitted into a sealed capacitor housing filled with electrolyte. One of the sets of anode tabs or cathode tabs, typically the anode cathode tabs, are coupled to an electrical feedthrough pin extending through the capacitor housing, and the other of the set of anode tabs or cathode tabs, typically the cathode tabs, are electrically connected to the capacitor housing, whereby the cathode housing is active.

The capacitor housing is shaped and dimensioned to snugly fit within and fill the volume within a particular portion of the ICD IPG housing. Early pacemaker IPGs were disk shaped and informally referred to as "hockey pucks" due to their similar diameter, thickness, and weight. Current pacemaker and ICD IPG housings are dramatically reduced in size, volume, and weight but retain the resemblance in certain respects. The housings of ICD IPGs as well as other IMDs that are to be implanted subcutaneously in the pectoral region continue to typically have opposed, nominally planar major surfaces joined by a continuous side wall that is typically flat along one segment of the edge to be fitted with or support the ICD IPG connector header and a filtered electrical feedthrough assembly. The remaining sidewall is rounded at the edges with the opposed, generally planar major surfaces so as to eliminate sharp 90° edges presented to subcutaneous tissue.

The flat electrolytic capacitor housings (as well as the battery housings) are shaped to fit the designated portions of the IPG housing. Therefore, the capacitor cases typically have generally opposed, substantially planar, major case sides joined by a continuous minor case side that maintains the opposed, substantially planar, major case sides substantially in parallel alignment, the minor case side defining the nominal height or thickness of the capacitor case. The capacitor case typically comprises a cover and a "can", each formed of a conductive housing material. The can typically has a top opening or a side opening to enable insertion of an electrode stack assembly of one of the types described above conforming in shape to the space within the can. The anode and cathode layers of the electrode stack assembly are electrically connected to anode and cathode terminals extending through the can, although the cathode layers can simply be coupled to the can. The case cover is welded to the can after anode and cathode terminal electrical connections are made, and electrolyte is injected into the space within the can through a fill port that is then closed. The resulting capacitor is electrically tested and aged, and some convex bulging of the substantially planar, major case sides can occur due to internal pressures. One approach to the packaging of the components of an ICD IPG including a single flat electrolytic capacitor is disclosed in U.S. Pat. No. 5,370,669. The flat batteries, electrolytic capacitor, and an electronic circuit module are sandwiched together using polymeric spacers, clips, shells, and retainers and frames. The capacitor housing is insulated on one major flat surface from the circuit module by a flat polyimide spacer and fitted into a polymeric retainer so that the other major surface and edge of the capacitor housing is electrically insulated from the ICD IPG housing and batteries.

Complex retainers and spacers are also employed in the above-referenced '910 patent to retain and electrically isolate the cylindrical capacitors from the other components of the ICD IPG. An electrical grounding shield within an outer liner is also interposed between the circuit module and other circuit interconnections and the ICD IPG housing to attenuate electromagnetic coupling and facilitate use of the ICD IPG housing as a cardioversion/defibrillation shock delivery electrode. The above-referenced '090 patent employs a heat shrinkable outer liner and grounding shield that is heat shrunk over the assembled components that are fitted into the ICD IPG housing.

A set of equivalent volume and capacitance flat or prismatic electrolytic capacitors having active capacitor cases are employed in many current ICD IPGs that are electrically connected in series to be charged to a high voltage as described in the commonly assigned above-referenced '133 patent. The capacitors can be made to be thin and mounted side-by-side. However, it is necessary to electrically insulate the facing sides of the electrically active capacitor cases from one another and other surfaces of the capacitor cases from the IPG housing and other electrical components. Therefore, the set of electrolytic capacitors are typically assembled into a capacitor sub-assembly having insulating layers between the capacitor sides facing one another and around the exposed surfaces of the set of capacitors. Such insulation packaging undesirably increases the bulk of the capacitor sub-assembly and the resulting bulk of the IPG housing.

One way of insulating the facing sides of the capacitor cases is to adhere an electrically insulating sheet between them. In one approach, a pre-cut, flat, planar sheet of a polymer, e.g., polyimide, is die cut into the overall shape of the capacitor sides with extensions adapted to be adhered to the side of the capacitor set. The polymer sheet has pressure sensitive adhesive layers deposited on each opposed surface that are protected by carrier papers until the sheet is used. In use, the carrier papers are removed, and the insulating sheet is carefully adhered to the capacitor sides and the extensions are folded over the capacitor case edges. Then, if any exposed insulating sheet remains, it can be manually trimmed away.

The pre-cut shape of the planar sheet does not conform to the features of the capacitor case major sides and the major side perimeters to be insulated from one another. The application of the insulating sheet must be carefully accomplished to avoid wrinkles or bunches and buckling when the perimeter of the planar sheet is wrapped around the radius. While the capacitor case major sides are nominally planar and parallel to one another, they can bulge out somewhat within prescribed tolerances as described above, leading to uneven spacing between the facing capacitor sides. The capacitor can is formed with a nominally 90° radius, in the bend at the perimeter of the capacitor can bottom (one of the capacitor case major sides) where the can bottom is joined with the capacitor case minor side in the can forming process. Wrinkling of the perimeter of the insulating sheet over the radius can cause edge buckling or bunching of the insulating sheet and can increase the overall volume of the capacitor sub-assembly, even if these irregularities are within defined tolerances. Consequently, it is necessary to set the dimensional tolerances of the capacitor sub-assembly and specify dimensions of the IPG housing and the capacitor retainer or spacer, if any, to be large enough to accommodate capacitor cases within the tolerances, adding to the bulk of the IPG housing. Moreover, capacitor sub-assemblies that fail to meet the tolerances must be reworked or scrapped, adding to expense.

In another approach, an insulating layer of vapor-deposited thin insulating film, (e.g., Parylene) or have been deposited on the sides of the capacitor case. This approach leads to inconsistent insulation and higher cost, higher manufacturing equipment maintenance, longer manufacturing process cycle times, etc.

Certain ICD IPGs have been powered by two batteries that have conductive cases that must be electrically isolated from mutual contact or from contact with the electronic circuit module or the capacitor case(s) as illustrated in the '669 patent. Relatively bulky polymeric retainers and spacers are also required to maintain this electrical isolation.

Thus, there is a need for further reducing capacitor sub-assembly volume, increasing capacitor sub-assembly dimensional uniformity, and reducing cost and complexity of the capacitor sub-assembly manufacturing process for such capacitor sub-assemblies used in ICD IPGs and other IMDs. There are similar continuing needs in the fabrication of battery sub-assemblies used in ICD IPGs and other IMDs.

SUMMARY OF THE INVENTION

The present invention provides for methods and apparatus for forming a component sub-assembly for assembly with other components of an ICD IPG into an IPG housing where the component sub-assembly comprises two or more components stacked side-by-side such that the facing component case major sides are separated by a reliable and simple to apply insulation layer of minimal thickness. Preferably, one or both of the exposed component case major sides are also insulated by a reliable and simple to apply insulation layer of minimal thickness.

In accordance with a first aspect of the present invention, a shape conforming insulating spacer is formed of an insulating material to conform to the shape of a first component case major side and the perimeter of that major side. The shape conforming insulating spacer is cup-shaped preferably having a concave spacer bottom conforming to any convex bulge in the first component case major side and a spacer side wall or rim conforming with the bend in the perimeter of the first component case major side.

In one embodiment, the interior surface of the shape conforming insulating spacer is simply applied against the mating surface of the first component case major side and maintained there by applied pressure during the final assembly of the component sub-assembly and/or by an electrostatic surface attraction of the material or by a wetting agent that forms a vapor-lock or the like.

In a further embodiment, the interior surface of the shape conforming insulating spacer is adhered with the surface of the first component case major side. The adhesive can be applied as an adhesive layer first either to the interior surface of the shape conforming insulating spacer or to the surface of the first component case major side. The shape conforming insulating spacer and first component case major side are then brought together with the adhesive layer between them and adhering them together. Then, the adhesive can be applied as an adhesive layer first either to the exterior surface of the shape conforming insulating spacer or to the surface of the second component case major side. The shape conforming insulating spacer adhered to the first component major side and the and second component case major side are then brought together with the adhesive between them and adhering them together.

The applied adhesive can add or contribute undesirable thickness to the assembly of the two components and the shape conforming insulating spacer. Consequently, it is preferable to thin the adhesive layer or to eliminate it in bulges or irregularities of the first and/or second major sides of the component cases that are joined together.

In one preferred alternative embodiment, a band or other pattern of adhesive is applied to the interior surface of the shape conforming insulating spacer such that a central portion of the interior and exterior surfaces of the spacer bottom are only thinly coated with adhesive or are substantially free of adhesive to minimize the thickness contribution of the adhesive. In this way, the thickness contribution of the adhesive layer in locations where any bulging of the facing component sides is likely to occur is minimized. The adhesive can be a liquid or self-levelling adhesive e.g., a contact cement or the like and is sprayed or painted all over the selected surfaces or in the above-described patterns on the selected surfaces.

Preferably the adhesive layer is formed of a pressure sensitive adhesive (PSA) layer applied manually or by other means to such surfaces in any of the orders described herein. The PSA layer preferably is provided in the form of a free-standing sheet of PSA protected on both sides by contact paper and cut to any of the shapes described herein. The contact paper is removed from one side of the PSA layer sheet, and the exposed PSA is adhered first to one of the surfaces to be joined. The contact paper is then removed from the other side of the PSA layer sheet, and the exposed PSA is adhered to the other of the surfaces to be joined.

The shape conforming insulating spacer can be placed between the facing major sides any further components that are stacked side-by-side in component sub-assemblies comprising three or more components.

Moreover, the shape conforming insulating spacers without any adhesive applied to the exterior surfaces of the spacer bottom can be adhered to the first component case major side at the end of the stack of components.

Advantageously, the assembly of the resulting component sub-assembly is simplified, and the possibility of errors made during assembly is reduced. The thickness of the resulting component sub-assembly is minimized and tolerances can be reduced. The thickness of the retainer, if any, for the component sub-assembly and the IPG housing can be minimized.

The present invention is preferably employed in the fabrication of, and as the resulting fabricated, capacitor sub-assemblies of a plurality of electrolytic capacitors or a battery sub-assembly of a plurality of batteries.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 7 is a perspective exploded view of the components of the electrolytic capacitor sub-assembly assembled following a first embodiment;

FIG. 8 is a perspective exploded view of the components of the electrolytic capacitor sub-assembly assembled following a second embodiment; and FIG. 9 is a perspective exploded view of the components of the electrolytic capacitor sub-assembly assembled following a further embodiment.

DETAILED DESCRIPTION OF THE PREFERRED EMBODIMENTS

The present invention is preferably employed in the fabrication of, and as the resulting fabricated, capacitor sub-assemblies of a plurality of electrolytic capacitors or a battery sub-assembly of a plurality of batteries.

Preferred embodiments of the present invention are described herein in relation to electrolytic capacitors assembled into a capacitor sub-assembly and fitted into IPG housing in accordance with the general principles of the invention. The ICD embodiment depicted in FIGS. 1 and 2 is simplified inasmuch as the present invention can be embodied into any IMD and is not limited to any particular ICD operating system or ICD IPG.

Figure 1:
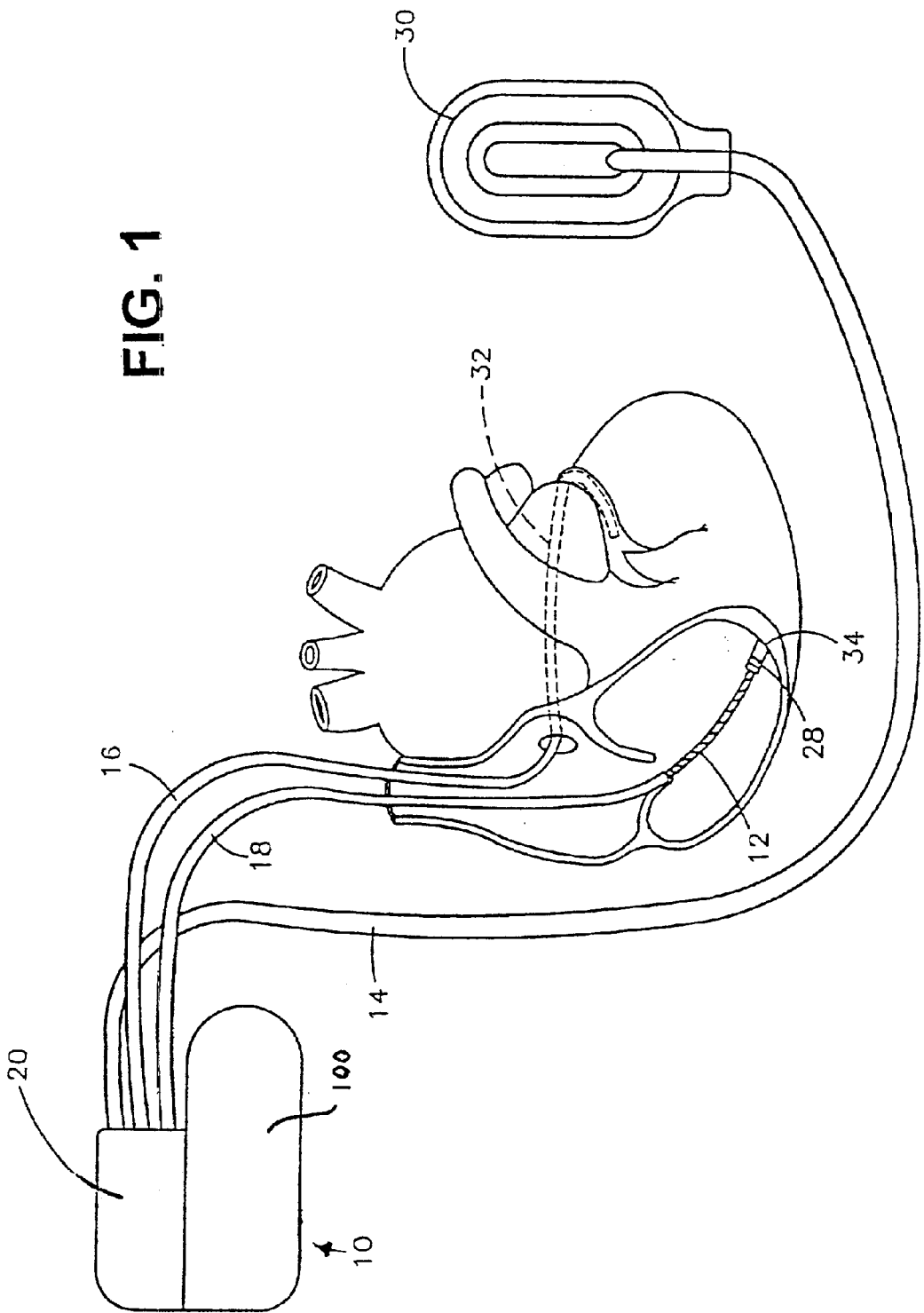
FIG. 1 illustrates the physical components of one exemplary embodiment of an ICD IPG and lead system in which the present invention may be advantageously incorporated.
Figure 2:
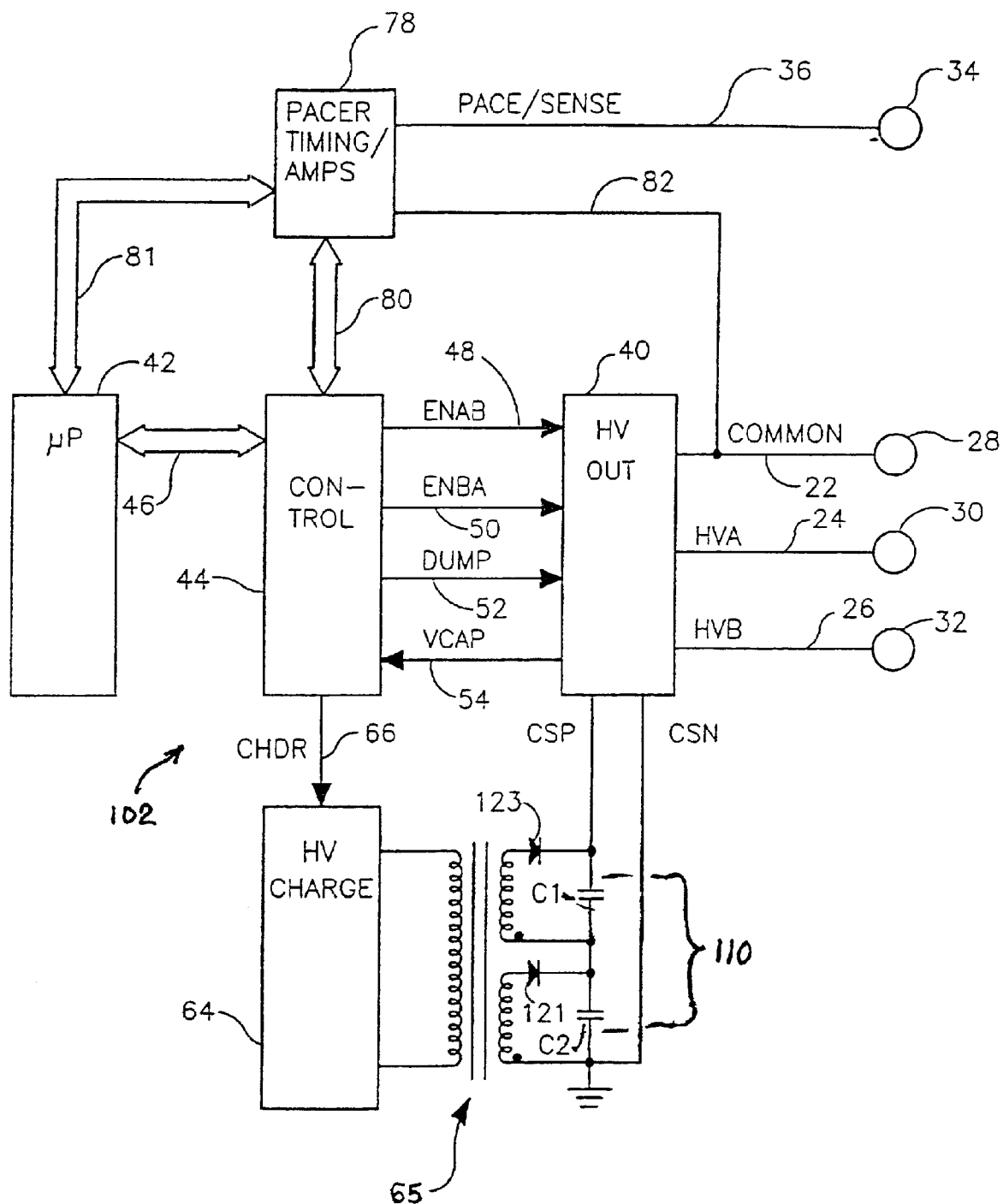
FIG. 2 is a simplified functional block diagram illustrating the interconnection of voltage conversion circuitry with the high voltage capacitors of the present invention with the primary functional components of one type of an ICD.

FIG. 1 therefore schematically illustrates an exemplary single chamber embodiment of an ICD comprising ICD IPG 10, in which the flat electrolytic capacitor sub-assembly of the present invention can be fitted, and the associated ICD electrical medical leads 14, 16 and 18 in relation to a human heart 12. The ICD IPG 10 comprises an IPG connector header 10 coupled to a hermetically sealed IPG housing 100. It will be noted that the schematic illustration of ICD IPG 10 is generalized, whereas a particular shape of the IPG housing 100 and its components are illustrated realistically in FIGS. 3 and 4. It will also be understood that the present invention can be employed in the methods of assembly and resulting sub-assembly of a plurality of flat electrolytic capacitors into an ICD IPG housing 100 of any configuration.

In FIG. 1, the leads 14, 16 and 18 are coupled to ICD IPG 10 by means of multi-port connector header 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode, which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28, which is located in the right ventricle of the heart. Lead 18 also includes stimulation electrode 34 that takes the form of a helical coil that is screwed into the myocardial tissue of the right ventricle. Lead 18 may also include one or more additional electrodes for near and far field electrogram sensing.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation shock regimens may be also provided, typically between electrode 28 and coronary sinus electrode 32. Alternatively, single pulses may be delivered between electrodes 28 and 30. The particular interconnection of the electrodes to the ICD circuitry will depend somewhat on which specific single electrode pair defibrillation shock regimen is believed more likely to be employed.

FIG. 2 is a highly simplified block diagram illustrating the interconnection of components contained within IPG housing 100 including the depicted electronic circuitry 102, a capacitor sub-assembly 110 comprising high voltage capacitors C1 and C2, a high voltage, high frequency, step-up transformer 65, and a battery (not shown) providing power to the electronic circuitry. The electronic circuitry includes pace/sense circuit 78, control circuit 44, high voltage output circuit 40, high voltage charging circuit 64, the microprocessor 42, and the various data and control conductors and buses. Other discrete components that can be included but are not shown include a telemetry antenna, a patient activity sensor, and an audible patient alarm, and these components are operated through further circuits within control circuit 44. The ICD operations are controlled by means of a stored program in microprocessor 42, which performs all necessary computational functions within the ICD, and the control circuit 44. Microprocessor 42 is linked to control circuit 44 by means of bi-directional data/control bus 46, and thereby controls operation high voltage charging circuit 64 in charging the high voltage capacitors C1 and C2 and of the high voltage output circuit 40 in discharging the high voltage capacitors C1 and C2.

Pace/sense circuit 78 awakens microprocessor 42 to perform any necessary mathematical calculations, to perform tachycardia and fibrillation detection procedures and to update the time intervals controlled by the timers in pace/sense circuit 78 on reprogramming of the ICD operating modes or parameter values or on the occurrence of signals indicative of delivery of cardiac pacing pulses or of the occurrence of cardiac contractions.

Control circuit 44 provides three signals of primary importance to output circuit 40. Those signals include the first and second control signals discussed above, labelled here as ENAB, line 48, and ENBA, line 50. The DUMP signal, line 52, initiates discharge of the output capacitors, and VCAP line 54 that provides a signal indicative of the voltage stored on the high voltage output capacitors C1, C2, to control circuit 44. Defibrillation electrodes 28, 30 and 32 illustrated in FIG. 1, above, are shown coupled to output circuit 40 by means of conductors 22, 24 and 26. For ease of understanding, those conductors are also labelled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrillation shock is delivered between electrode 30 and electrode 28. During a logic signal on ENBA, line 50, a cardioversion/defibrillation shock is delivered between electrode 32 and electrode 28.

The high voltage charging circuit includes the capacitor sub-assembly 110, including capacitors C1 and C2, step-up transformer 65, diodes 121 and 123, and high voltage charging circuit 64. Proper charging polarities are maintained by means of the diodes 121 and 123. Capacitors C1, C2 are charged through the transformer and diodes 121,123 to a high voltage by operation of high voltage charging circuit 64 under the control of the control/timing circuit 44 via CHDR line 66. VCAP line 54 provides a signal indicative of the voltage on the capacitors C1, C2 to control circuit 44 that terminates the charging function when the measured voltage equals the programmed charging level.

Pace/sense circuit 78 includes an R-wave sense amplifier and a pulse generator for generating cardiac pacing pulses, which may also correspond to any known cardiac pacemaker output circuit and includes timing circuit for defining ventricular pacing intervals, refractory intervals and blanking intervals, under control of microprocessor 42 via control/data bus 80.

Control signals triggering generation of cardiac pacing pulses by pace/sense circuit 78 and sense event signals indicative of the occurrence of R-waves in this particular example, from pace/sense circuit 78 are communicated to control circuit 44 by means of a bi-directional data bus 81. Pace/sense circuit 78 is coupled to helical electrode 34 illustrated in FIG. 1 by means of a conductor 36. Pace/sense circuit 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

Figure 3:
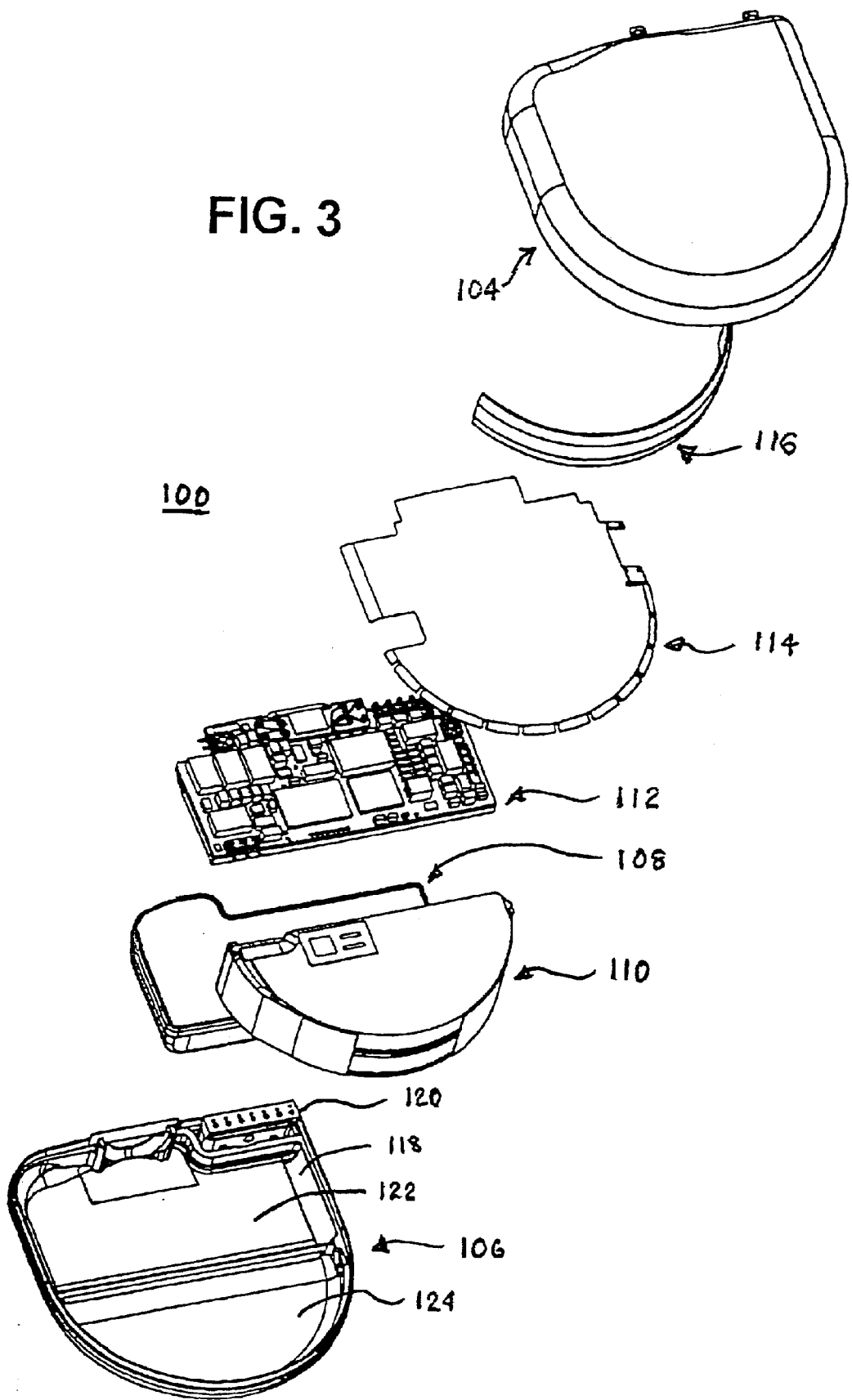
FIG. 3 is an exploded perspective view of the manner in which the various components of the exemplary ICD IPG of FIGS. 1 and 2, including the electrolytic capacitor sub-assemblies of the present invention, are disposed within the housing of the ICD IPG.
Figure 4:
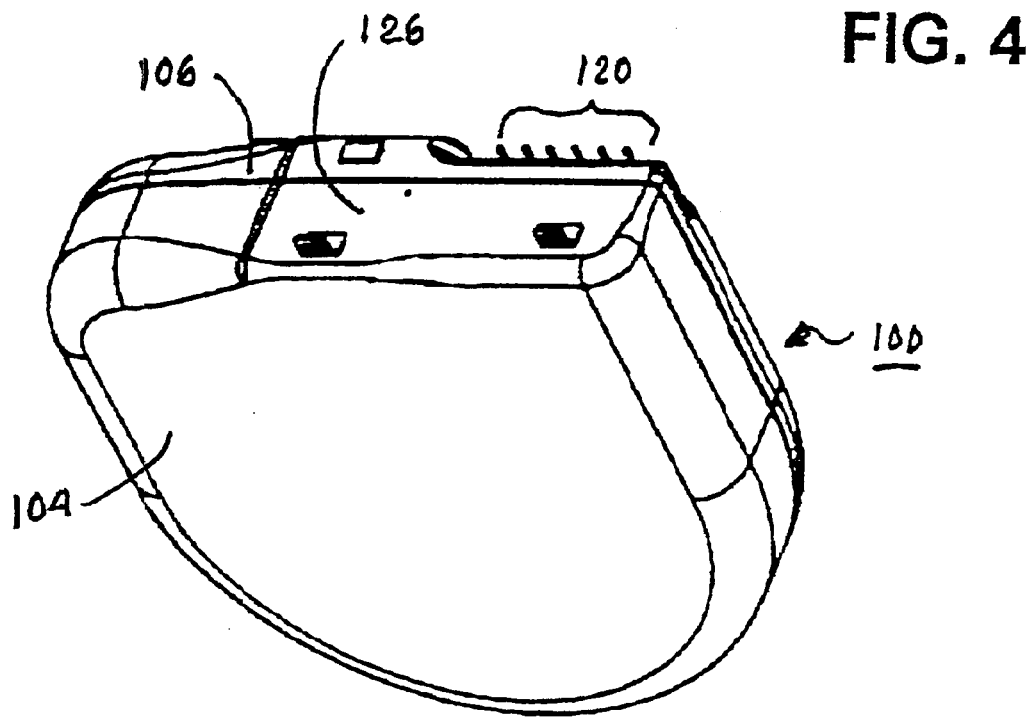
FIG. 4 is a perspective view of the IPG housing after the components of FIG. 3 are assembled into the IPG housing cavity.

The physical shapes of the major components of FIG. 2 are depicted in the perspective view of FIG. 3 together with other components that form to the IPG housing 100 when assembled as shown in FIG. 4. The IPG housing 100 comprises first shield half 104 and a second shield half 106 that are adapted to be welded together and attached to the connector header 20 when the other components depicted in FIG. 3 are inserted into cavities of the first shield half 104 and the second shield half 106 and electrically connected together. The integrated circuitry 102, diodes 121, 123, and transformer 65 described above are fabricated into a hybrid circuit module 112. The depicted components further include a flex circuit 114 preferably incorporating a patient alert transducer and antenna as well as interconnecting circuits, a dessicant liner 116 formed of a dessicant material in a molded silicone matrix that absorbs moisture and one or more insulating and shock absorbing polymeric liner or cup inserted into the shield half 104 and shield half 106, e.g., cup 118 shown fitted into shield half 106. Shield half 106 also supports a capacitive filtered feedthrough array 120 that provides filtered and electrically isolated electrical connections with connector elements in the connector header 20.

The cup 118 is shaped with a receptacle 122 into which the battery 108 is fitted and a further receptacle 124 into which the capacitor sub-assembly 110 is fitted. The hybrid circuit module 112 is fitted over the battery 108, the dessicant liner 116 is fitted between a portion of the capacitor sub-assembly minor side wall and the inside of shield half components 104 and 106, and the flex circuit 114 is fitted over the capacitor sub-assembly 110 and the hybrid circuit module 112. Electrical connections are made between terminals of the components and the feedthrough array 120 as the components are fitted together. The assembled ICD IPG housing 100 shown in FIG. 4 presents a substantially flat surface 126 against which a connector header 20 is attached and coupled with the feedthrough pins of the filtered feedthrough array 120.

Minimizing the dimensions and resulting volume of the assembled hermetically sealed IPG housing 100 shown in FIG. 4 is dependent upon a number of factors. One primary factor is the required maximum high voltage shock capability that is necessary to effectively defibrillate patient's hearts. That capability depends in turn upon capabilities of the battery 108 providing the charging energy over a suitable IPG lifetime, the charging current handling capabilities of the charging circuit components, and the capacitance of the capacitors C1, C2 of the capacitor sub-assembly 110. These components have been reduced in size considerably over the years since ICDs were first fabricated and implanted in human patients. Numerous improvements have been made to the flat electrolytic capacitors to increase capacitance and current handling capabilities thereby allowing them to be reduced in size substantially. Similarly, battery technologies and fabrication techniques have decreased battery volume and increased the battery life substantially.

Figure 5:
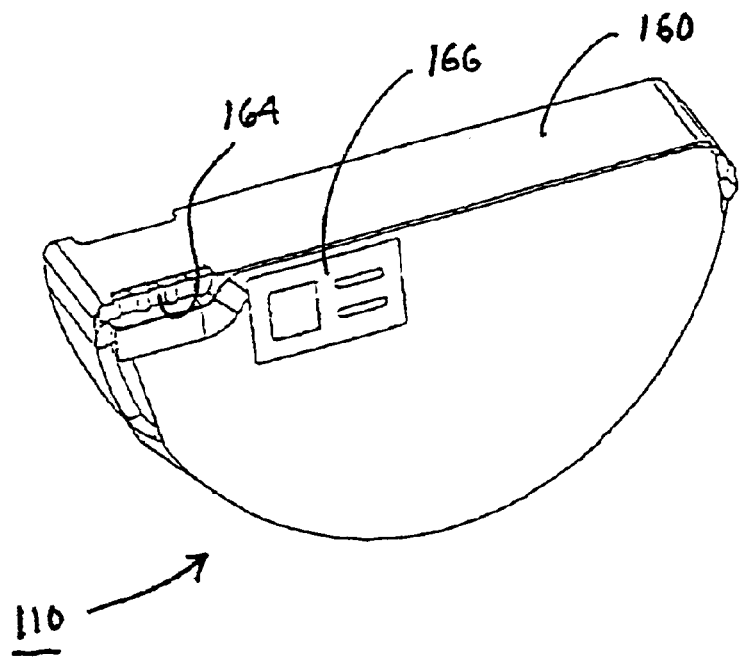
FIG. 5 is a perspective view of the capacitor sub-assembly assembled from the components of the present invention.

The present invention provides for methods and apparatus for forming the capacitor sub-assembly 110 depicted in FIG. 5 for assembly with other components of the ICD IPG into the IPG housing 110 with decreased thickness of insulation between the two (or more) electrolytic capacitors C1, C2, (Cn) stacked side-by-side. The facing capacitor case major sides are separated by a reliable and simple to apply insulation layer of minimal thickness. Preferably one or both of the exposed capacitor case major sides are also insulated by a reliable and simple to apply insulation layer of minimal thickness.

Figure 6:
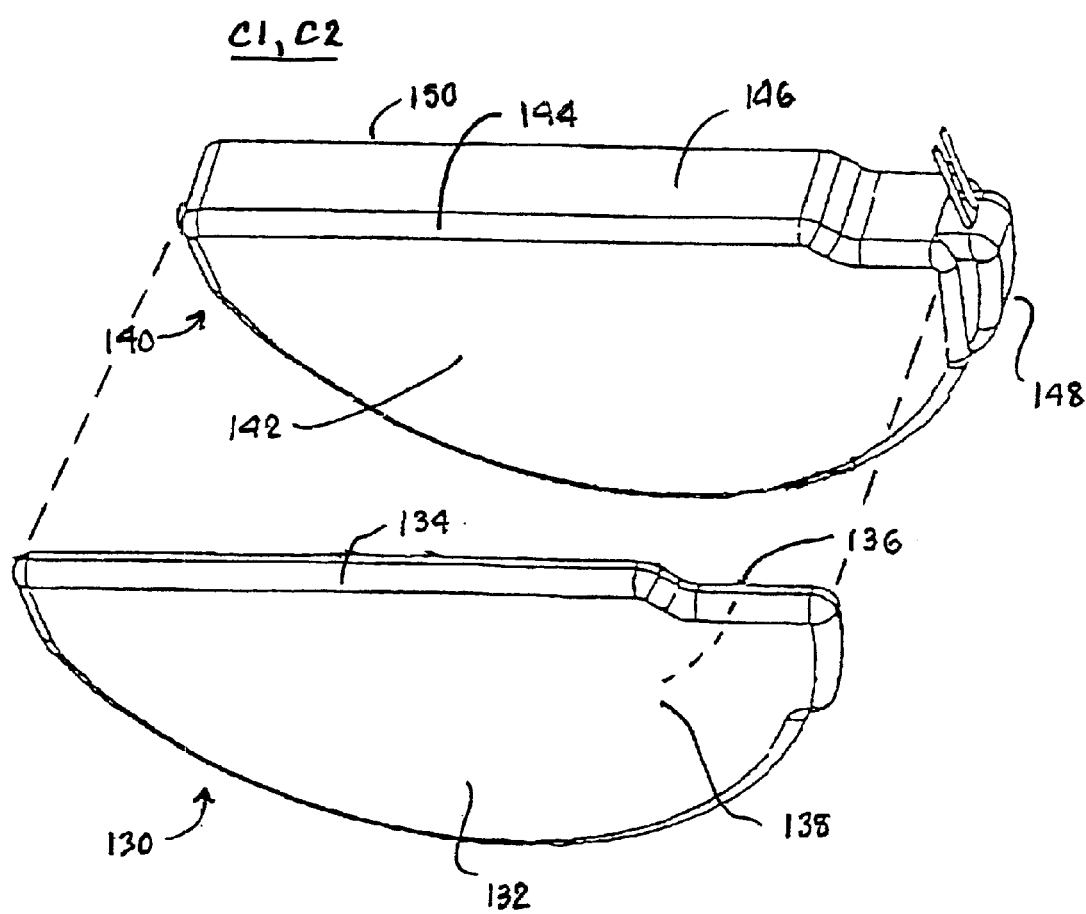
FIG. 6 is a perspective view of the shape conforming insulating spacer shaped to conform to the capacitor case major side of the capacitor.

Turning to FIG. 6, in accordance with a first aspect of the present invention, a shape conforming insulating spacer 130 is formed of an insulating material to conform to the shape of a first capacitor case major side 142 of capacitor case 140 and the perimeter 144 of that major side 142. The capacitor case 140 of capacitor C1, C2 has generally opposed, substantially planar, major case sides 142 and 150 (obscured from direct view) joined by a continuous minor case side 146 that maintains the opposed, substantially planar, major case sides 142 and 150 substantially in parallel alignment. The minor case side 146 defines the nominal height or thickness of the capacitor case 140. The capacitor case 140 comprises a cover and a can formed of a conductive material, and the cover in this example is the major case side 150. The can in this example comprises the substantially planar major case side 142, the minor side wall 146, and the 90° radius bend mutual periphery 144 joining the major case side 142, the minor side wall 146.

The capacitor case 140 encloses an anode and cathode assembly of any configuration. The anode and cathode assembly may comprise the electrode stack assembly of the type described in the above-referenced '133 patent, for example, composed of anode layers and cathode layers separated by a separator conforming in shape to the space within the can. The anode and cathode layers are electrically connected to anode and cathode terminals that extend from the capacitor connector assembly 148 by way of anode and cathode feedthrough pins of feedthroughs affixed through the wall of the minor case side 146 case and attached to the anode and cathode layers. Alternatively, the cathode layers are simply coupled to the capacitor case 140 rather than a cathode feedthrough pin wherein the cathode terminal is welded to the capacitor case 140 within the capacitor connector assembly 148. The case cover is welded to the can after the anode and cathode electrical connections are made, thereby forming the second capacitor case major side 150, and electrolyte is injected into the space within the can through a fill port that is then closed.

The resulting capacitor is electrically tested and aged, and some convex bulging of the substantially planar, major case sides can occur due to pressures within the case. Thus, while the major capacitor sides 142, 150 of the capacitor case 140 are nominally planar, they can bulge out somewhat within prescribed tolerances, leading to uneven spacing between the facing capacitor sides. The bulging out is most pronounced toward the centers of the major capacitor sides 142, 150.

In this example, the capacitor case 140 is formed with a nominally 90° radius bend at perimeter 144 of the first capacitor case major side 142 where the capacitor case major sides 142 and 150 are joined together with and by the capacitor case minor side 146. This perimeter 144 is where the buckling or bulging of the planar insulating sheet can occur causing the overall volume of the capacitor sub-assembly to increase. Consequently, it has been necessary to set the dimensional tolerances of the volume of the capacitor sub-assembly 110 and specify volume dimensions of the IPG housing 100 and the capacitor retainer or cup 118 to be large enough to accommodate capacitor cases 140 and insulating spacers within the tolerances, adding to the bulk of the IPG housing 100.

The shape conforming insulating spacer 130 depicted in FIG. 6, is cup-shaped having a concave spacer bottom 132 conforming to a nominal convex bulge in the first capacitor case major side 142 and a spacer side wall or rim 134 conforming with the bend in the perimeter 144 of the first capacitor case major side 142. The insulating spacer 130 thus presents an inner surface 136 (obscured in FIG. 6) and an outer surface 138.

The shape conforming insulating spacer 130 is formed of a polymer, e.g., polyimide or polyamide that is cast to a nominal dimension model or mold form of the first major case side 142 and the periphery 144 of the can by one of injection molding, thermoforming, vacuum forming, stereolithography, blow molding, etc. The fabricated shape conforming insulating spacer 130 must be free of pinholes and have sufficiently high dielectric withstand voltage properties.

Preferably, the shape conforming insulating spacer 130 is formed from polyimide (or other insulating materials) through a thermoforming process that relies on the use of both heat and pressure to deform a thermoplastic material into a predetermined shape, and the resulting product is sometimes called a "thermoform". The heat may be provided by the mold itself, a preheater, or an extruder (not shown specifically). In any event, a polymeric web is heated sufficiently to permit thermoforming. The temperature to which the polymeric web must be heated varies over a broad range (i.e., about 200° F.–550° F.) depending on the gauge and type of material that is being thermoformed as well as the speed of the manufacturing line. The applied pressure is sufficient to permit a high quality replication of the mold or die pattern and may be provided by, for example, the force the mold exerts upon the web when the mold closes, or by the application of a vacuum that urges the web to deform over a male die or draws the web into a female die (i.e., vacuum thermoforming). The web is typically cooled after thermoforming, which can be accomplished by air cooling, fans, a water bath or a cooling oven until the thermoplastic polymer solidifies.

In general, thermoforming is a process that is familiar to those of ordinary skill in the art and is described in various references, such as the *Encyclopedia of Polymer Science and Engineering*, volume 16, second edition, published by John Wiley & Sons, 1989, which discusses different thermoforming processes and the use of roll-fed, sheet-fed, in-line extrusion, and continuous web-fed systems. All of these can be employed to manufacture the shape conforming insulating spacer 130 of the invention, as can different thermoforming tools that are described in the technical literature, such as flat forming and rotary devices, these devices being available for use with various thermoforming techniques such as matched mold forming, plug-assist forming, basic vacuum forming, and pressure forming.

In the formation of a capacitor sub-assembly 110, at least two flat electrolytic capacitors 140 are stacked face-to-face with the first capacitor case major side 142 of a first electrolytic capacitor C1 facing the second capacitor case major side 150 of a second electrolytic capacitor C2. An insulating spacer 130 is disposed between the facing first capacitor case major side 142 of the first electrolytic capacitor C1 and the second capacitor case major side 150 of the second electrolytic capacitor C2. The inner surface 136 is disposed against the first capacitor major case side 142 of first electrolytic capacitor C1, and the outer surface 138 is disposed the second capacitor case major side 150 of second electrolytic capacitor C2. Optionally, the inner surface 136 of a further insulating spacer 130 is disposed against the first capacitor major case side 142 of the second electrolytic capacitor C1. Further electrolytic capacitors C3 . . . Cn and insulating spacers 130 can be stacked with capacitors C1, C2 in this manner. The capacitor sub-assembly 110 further includes a mechanism to hold the stacked plurality N of electrolytic capacitors C1 . . . Cn and spacers $130_1$ . . . . $130_N$ together and in registration.

A first embodiment of a capacitor sub-assembly 110 is depicted in FIG. 7. The shape conforming insulating spacers $130_1$ and $130_2$ are simply applied against the surfaces of the first capacitor case major sides 142 of the first and second capacitor cases 140 and maintained there during the final assembly of the capacitor sub-assembly 110. The final assembly includes coupling the anode and cathode terminals of each capacitor C1, C2 with capacitor connector element 164, taping the capacitors C1, C2 together using a perimeter electrical insulating tape 160, and applying a part label 166 to the first capacitor C1.

The electrical connector element 164 is preformed of insulating material supporting printed circuits and pads for attachment with the ICD hybrid circuit module 112 and fits into the recess of two (or more if its features are replicated) side-by-side assembled capacitor cases. First, double sided adhesive tape 162 is applied against side-by-side portions of the capacitor case minor sides adjacent to the capacitor connector assembly 148 of the capacitors C1, C2. The anode and cathode terminals or feedthrough pins of each capacitor C1, C2 are fitted into side-by-side slots of the capacitor terminal 164 and welded to pads in side-by-side slots of the printed circuit board capacitor terminal 164 to make electrical connection with a printed circuit in each case. The terminal pins bend over as a lower surface of the capacitor terminal 164 is applied against the exposed surface of double sided adhesive tape 162 to adhere the capacitor terminal 164 thereto. The perimeter electrical insulating tape 160 is applied over the capacitor terminal 164 and the majority or all of the side-by-side aligned capacitor case minor sides of capacitors C1, C2. The pads of the electrical connector element 164 are coupled with the ICD hybrid circuit module 112 when the assembly depicted in FIG. 3 is completed.

In this first embodiment, the shape conforming insulating spacers $130_1$ and $130_2$ are maintained in place by applied pressure and/or by an electrostatic surface attraction between the inner surface 136 of each shape conforming insulating spacer $130_1$ and $130_2$ and the first capacitor major side 142 and perimeter 144 of each of the first and second capacitors C1 and C2, respectively. Or a wetting agent can be applied to the inner surface 136 of each shape conforming insulating spacer $130_1$, and $130_2$ that forms a vapor-lock with the first capacitor major side 142 and perimeter 144 of each of the first and second capacitors C1 and C2, respectively.

In a further embodiment of fabrication of a capacitor sub-assembly 110' illustrated in FIG. 8, the interior surface 136 of the shape conforming insulating spacer $130_1$ is adhered by an adhesive layer 170 with the surface of the first component case major side 142 of capacitor C1 and the exterior surface 138 of the shape conforming insulating spacer $130_1$ is adhered by an adhesive layer 172 with the surface of the second component case major side 150 of capacitor C2. Preferably, an adhesive layer 174 is applied between the interior surfaces 136 of the shape conforming insulating spacer $130_2$.

The adhesive layers 170, 172, and 174 can be a liquid or self-levelling adhesive, e.g., a contact cement or the like, that is sprayed or painted or otherwise applied over the facing surfaces. The adhesive layer 170 can be applied to one or both of the surface of the first component case major side 142 of capacitor C1 and the interior surface 136 of shape conforming insulating spacer $130_1$, and the facing surfaces are then brought together. The adhesive layer 172 can be applied to one or both of the surface of the second component case major side 150 of capacitor C2 and the exterior surface 138 of the shape conforming insulating spacer $130_1$, and the surfaces are then brought together. The adhesive layer 174 can be applied to one or both of the surface of the first component case major side 142 of capacitor C2 and the interior surface 136 of the shape conforming insulating spacer $130_2$, and the surfaces are then brought together.

Preferably, the adhesive layers 170, 172, 174 are formed of a pressure sensitive adhesive (PSA) acrylic adhesive layers (also denoted 170, 172, 174 for convenience) applied manually or by other means to such surfaces in any order. Moreover, preferably the PSA layers 170, 172, 174 are provided in the form of free-standing sheets of PSA protected on both sides by contact paper and cut to any of the shapes described herein. The contact paper is removed from one side of the PSA layer sheet, and the exposed PSA is adhered first to one of the surfaces to be joined. The contact paper is then removed from the other side of the PSA layer sheet, and the exposed PSA is adhered to the other of the surfaces to be joined.

For example, the paper is removed from one side of the PSA layer 170, and that side is adhered to the first capacitor case major side 142 of the first capacitor C1. The paper coating is removed from the outer side of PSA layer 170, and the interior surface 136 of the shape conforming insulating spacer $130_1$ is pressed against the exposed PSA layer 170 so that the shape conforming insulating spacer $130_1$ is evenly adhered thereto by the interposed adhesive layer 170.

The paper is removed from one side of the PSA layer 172, and that side is adhered to the second capacitor case major side 150 of the second capacitor C2. The paper coating is removed from the outer side of PSA layer 172, and the second capacitor case major side 150 of the second capacitor C2 is pressed against the outer side of the PSA layer 172 adhesive layer 172.

Similarly, the paper is removed from one side of the PSA layer 174, and that side is adhered to the first capacitor case major side 142 of the second capacitor C2. The paper coating is removed from the outer side of PSA layer 174, and the interior surface 136 of the shape conforming insulating spacer $130_2$ is pressed against the exposed PSA layer 174 so that the shape conforming insulating spacer $130_2$ is evenly adhered thereto by the interposed adhesive layer 174.

The applied adhesive layers 170, 172, 174 can add or contribute undesirable thickness to the assembly of the two capacitors C1, C2 and the shape conforming insulating spacers $130_1$ and $130_2$. Consequently, it may be desirable to eliminate the adhesive layer 172 and depend upon the perimeter adhesive tape 160 to maintain the capacitors C1 and C2 in the capacitor sub-assembly 110'.

In a preferred alternative embodiment of a capacitor sub-assembly 110'' illustrated in FIG. 9, the adhesive is applied in any of the ways described above with respect to FIG. 8 as peripheral adhesive bands 180, 182, 184 such that a central portion of the interior and exterior surfaces 136 and 138 of the spacer bottom 132 are only thinly coated with adhesive or are substantially free of adhesive to minimize the thickness contribution of the adhesive in that central region. In this way, the thickness contribution of the adhesive in locations where any bulging of the facing capacitor major sides is likely to occur is minimized.

Again, the adhesive band 182 can be eliminated to reduce thickness. In addition, the widths of the bands 180 and 184 can be such that the adhesive only adheres the perimeters 142 of the capacitors C1, C2 to the rim band of the interior surface 138 fitted over the perimeters 142.

Moreover, it will be understood that other patterns of adhesive than the depicted adhesive bands 180, 182, 184, such as spots or patches or a horseshoe shape, can be substituted where the patterns are selected to avoid high spots and bulges in the face-to-face capacitor major sides 142 and 150 of capacitors C1 and C2 and on the first capacitor major side 142 of capacitor C2.

The fabrication steps do not require any trimming or bending of the edges of the shape conforming insulating spacers $130_1$ and $130_2$. Therefore, no lapping of edge material or trimming debris is generated that could inadvertently stick to the adhesive. The invention advantageously simplifies the assembly and inspection steps and rework and therefore reduces costs. And, the thickness contribution of the insulation between the capacitors C1 and C2 and against the first capacitor major side of capacitor C2 is minimized.

It will be understood that other means than the perimeter adhesive tape 160 can be employed to insulate and hold the first and second capacitors C1 and C2 together (or any plurality of such capacitors), e.g., preformed plastic cups or clamps or the like. Or, the shape conforming insulating spacer $130_2$ could be fabricated having a rim that extends over the sides of the first and second capacitors C1 and C2 to provide the electrical insulation and enhanced attachment of capacitors C1 and C2 together.

The preceding specific embodiments are illustrative of the structures and methods of fabrication of a capacitor sub-assembly of two or more electrolytic capacitors and its incorporation into an ICD IPG in accordance with the present invention employing specified components and materials. It is to be understood, therefore, that other components and materials known to those skilled in the art or disclosed herein, and existing prior to the filing date of this application or coming into existence at a later time, may be employed without departing from the invention or the scope of the appended claims.

Furthermore, it will be understood that the principles of the present invention can be employed in the fabrication of sub-assemblies of two or more batteries shaped in the manner described above with respect to capacitors C1 and C2.

In the claims, means-plus-function clauses are intended to cover the structures described herein as performing the recited function and not only structural equivalents but also equivalent structures.

All patents and printed publications disclosed herein are hereby incorporated by reference herein into the specification hereof, each in its respective entirety.

We claim:

1. An implantable medical device of the type comprising a housing having a housing cavity enclosing a plurality of like electrical components assembled into an electrical component sub-assembly, wherein the electrical component sub-assembly further comprises:

first and second electrical components, each electrical component comprising a electrical component case comprising first and second generally opposed, electrical component case major sides joined together through a continuous electrical component case minor side that maintains the first and second electrical component case major case sides substantially in parallel alignment, whereby the junction of the first electrical component case major side with the electrical component case minor side defines a perimeter having a bend radius;

a shape conforming insulating spacer of an insulating material interposed between the major sides of the electrical components, respectively, the shape conforming insulating spacer having a spacer bottom shaped to conform to the shape of the first electrical component case major side of the first electrical component and a spacer rim shaped to conform with the bend in the perimeter of the first electrical component case major side of the first electrical component; and means contacting at least portions of the continuous minor case sides of the electrical component cases for maintaining the sub-assembly of the electrical components with the shape conforming insulating spacer interposed therebetween.

2. The implantable medical device of claim 1, wherein the first electrical component case major side exhibits a convex bulge and the shape conforming insulating spacer is cup-shaped having a concave spacer bottom conforming to the convex bulge in the first electrical component case major side.

3. The implantable medical device of claim 1, wherein the shape conforming insulating spacer has an interior surface applied against the first electrical component case major side and perimeter of the first electrical component and an exterior surface.

4. The implantable medical device of claim 3 wherein the interior surface is maintained in contact with the first electrical component case major side and perimeter by applied pressure during the final assembly of the electrical component sub-assembly.

5. The implantable medical device of claim 3 wherein the interior surface is maintained in contact with the first electrical component case major side and perimeter by an electrostatic surface attraction of the insulating polymer to the electrical component case major side and perimeter.

6. The implantable medical device of claim 3 wherein the interior surface is maintained in contact with the first electrical component case major side and perimeter by a wetting agent that forms a vapor-lock between the interior surface and the first electrical component case major side and perimeter.

7. The implantable medical device of claim 3, further comprising an adhesive layer between substantially all of the interior surface and substantially all of the first electrical component case major side and perimeter of the first electrical component that adheres the interior surface to the first electrical component case major side and perimeter of the first electrical component.

8. The implantable medical device of claim 7, wherein the adhesive is a pressure sensitive adhesive.

9. The implantable medical device of claim 7, wherein the adhesive layer has a first thickness in a band extending inward from the rim and a second thickness less than the first thickness in a centrally disposed portion of the interior surface.

10. The implantable medical device of claim 9, wherein the adhesive is a pressure sensitive adhesive.

11. The implantable medical device of claim 3, further comprising an adhesive applied in a peripherally disposed adhesive pattern between the interior surface and the first electrical component case major side perimeter of the first electrical component that adheres the interior surface to the first electrical component case perimeter of the first electrical component.

12. The implantable medical device of claim 11, wherein the adhesive is a pressure sensitive adhesive.

13. The implantable medical device of claim 11, wherein the peripherally disposed adhesive pattern is a band extending inward from the rim of the shape conforming insulating spacer.

14. The implantable medical device of claim 13, wherein the peripherally disposed adhesive band is confined substantially to the interior surface of the rim of the shape conforming insulating spacer.

15. The implantable medical device of claim 13, wherein the adhesive is a pressure sensitive adhesive.

16. The implantable medical device of claim 3, further comprising an adhesive layer applied between at least a portion of the exterior surface of the shape conforming insulating spacer and the second electrical component case major side of the second electrical component.

17. The implantable medical device of claim 16, wherein the adhesive is a pressure sensitive adhesive.

18. The implantable medical device of claim 3, further comprising an adhesive applied in a peripherally disposed adhesive pattern between the exterior surface of the shape conforming insulating spacer and the exterior surface to the second electrical component case of the second electrical component.

19. The implantable medical device of claim 18, wherein the peripherally disposed adhesive pattern is a band extending inward from the rim of the shape conforming insulating spacer.

20. The implantable medical device of claim 1, further comprising a further shape conforming insulating spacer of an insulating material interposed against the first electrical component case major side of the second electrical component, the shape conforming insulating spacer having a spacer bottom shaped to conform to the shape of the first electrical component case major side and a spacer rim shaped to conform with the bend in the perimeter of the first electrical component case major side.

21. The implantable medical device of claim 20, wherein the first electrical component case major side of the second electrical component exhibits a convex bulge, and the further shape conforming insulating spacer is cup-shaped having a concave spacer bottom conforming to the convex bulge in the first electrical component case major side of the second electrical component.

22. The implantable medical device of claim 1, wherein the electrical component sub-assembly comprises first and second capacitors, each capacitor comprising:

a capacitor case comprising first and second generally opposed, capacitor case major case sides joined together through a continuous capacitor case minor side that maintains the first and second capacitor case major case sides substantially in parallel alignment, whereby the junction of the first capacitor case major side with the capacitor case minor side defines a perimeter having a bend radius;

an anode and cathode assembly comprising at least one anode, one cathode, a separator interposed between the anode and cathode and electrolyte disposed within the capacitor case; and anode and cathode terminals coupled with the respective anode and cathode for making electrical connection with the interconnecting circuitry.

23. A method of fabricating a electrical component sub-assembly for an implantable medical device of the type comprising a housing having a housing cavity enclosing components including an electronic circuit module, a battery, the electrical component sub-assembly, and circuitry interconnecting the electronic circuit module, battery and the electrical component sub-assembly, the method comprising:

fabricating first and second electrical components, each electrical component comprising an electrical component case enclosing an anode and cathode assembly and supporting anode and cathode terminals, each electrical component case comprising first and second generally opposed, electrical component case major case sides joined together through a continuous electrical component case minor side that maintains the first and second electrical component case major case sides substantially in parallel alignment, whereby the junction of the first electrical component case major side with the electrical component case minor side defines a perimeter having a bend radius;

fabricating a shape conforming insulating spacer of an insulating material, the shape conforming insulating spacer having a spacer bottom shaped to conform to the shape of the first electrical component case major side of the first electrical component and a spacer rim shaped to conform with the bend in the perimeter of the first electrical component case major side of the first electrical component;

interposing the shape conforming insulating spacer between the first and second major sides of the first and second electrical components, respectively; and coupling at least portions of the continuous minor case sides of the first and second electrical component cases for maintaining the sub-assembly of the first and second electrical components with the shape conforming insulating spacer interposed therebetween.

24. The method of claim 23, wherein the first electrical component case major side exhibits a convex bulge and the shape conforming insulating spacer fabricated in the step of fabricating the shape conforming insulating spacer is cup-shaped having a concave spacer bottom conforming to the convex bulge in the first electrical component case major side.

25. The method of claim 23, wherein the shape conforming insulating spacer comprises an interior surface adapted to be applied against the first electrical component case major side and perimeter in the interposing step and an exterior surface.

26. The method of claim 25, wherein the interior surface is maintained in contact with the first electrical component case major side and perimeter by applied pressure following the interposing step.

27. The method of claim 25, wherein the interior surface is maintained in contact with the first electrical component case major side and perimeter following the interposing step by an electrostatic surface attraction of the insulating polymer to the electrical component case major side and perimeter.

28. The method of claim 25, wherein the interior surface is maintained in contact with the first electrical component case major side and perimeter following the interposing step by a wetting agent that forms a vapor-lock between the interior surface and the first electrical component case major side and perimeter.

29. The method of claim 25, wherein the interposing step further comprises applying an adhesive layer between substantially all of the interior surface of the shape conforming insulating spacer and the first electrical component case major side and perimeter of the first electrical component.

30. The method of claim 25, wherein the interposing step further comprises applying a pressure sensitive adhesive layer between substantially all of the interior surface of the shape conforming insulating spacer and the first electrical component case major side and applying pressure between the first electrical component case major side and the shape conforming insulating spacer to adhere the interior surface to the first electrical component case major side and perimeter of the first electrical component.

31. The method of claim 25, wherein the interposing step further comprises applying an adhesive layer over the first electrical component case major side in a first thickness in a band extending inward from the rim and in a second thickness less than the first thickness in a centrally disposed portion of the interior surface that adheres the interior surface to the first electrical component case major side and perimeter of the first electrical component.

32. The method of claim 25, wherein the interposing step further comprises:

applying a pressure sensitive adhesive layer between the interior surface and the first electrical component case major side, the pressure sensitive adhesive layer having a first thickness in a band extending inward from the rim and in a second thickness less than the first thickness in a centrally disposed portion of the interior surface; and applying pressure between the first electrical component case major side and the shape conforming insulating spacer to adhere the interior surface to the first electrical component case major side and perimeter of the first electrical component.

33. The method of claim 25, wherein the interposing step further comprises applying an adhesive layer between the interior surface and the first electrical component case major side and perimeter of the first electrical component in a peripherally disposed adhesive pattern that adheres the interior surface to the first electrical component case perimeter of the first electrical component.

34. The method of claim 33, wherein the peripherally disposed adhesive pattern is a band extending inward from the rim of the shape conforming insulating spacer.

35. The method of claim 34, wherein the peripherally disposed adhesive band is confined substantially to the interior surface of the rim of the shape conforming insulating spacer.

36. The method of claim 23, wherein the interposing step further comprises applying an adhesive layer between at least a portion of the exterior surface of the shape conforming insulating spacer and the exterior surface to the second electrical component case major side of the second electrical component.

37. The method of claim 23, wherein the interposing step further comprises applying an adhesive layer between a peripheral portion of the exterior surface of the shape conforming insulating spacer and a peripheral portion of the second electrical component case major side of the second electrical component.

38. The method of claim 23, wherein the interposing step further comprises:
  applying a pressure sensitive adhesive layer between at least a portion of the exterior surface of the shape conforming insulating spacer and the second electrical component case major side of the second electrical component; and
  applying pressure between the second electrical component case major side and the shape conforming insulating spacer to adhere the exterior surface to second electrical component case major side of the second electrical component.

39. The method of claim 23, further comprising:
  fabricating a further shape conforming insulating spacer of an insulating material having an interior surface and an exterior surface of a spacer bottom shaped to conform to the shape of the first electrical component case major side and a spacer rim shaped to conform with the bend in the perimeter of the first electrical component case major side of the second electrical component; and
  applying the interior surfaces of the further shape conforming insulating spacer against the first electrical component case major side and perimeter of the second electrical component.

40. The method of claim 23, wherein the first electrical component case major side of the second electrical component exhibits a convex bulge, and further comprising:
  fabricating a further shape conforming insulating spacer of an insulating material having an interior surface and an exterior surface of a spacer bottom shaped to conform to the convex bulge of the first electrical component case major side and a spacer rim shaped to conform with the bend in the perimeter of the first electrical component case major side of the second electrical component; and
  applying the interior surfaces of the further shape conforming insulating spacer against the first electrical component case major side and perimeter of the second electrical component.

41. The method of claim 23, further comprising:
  fabricating a further shape conforming insulating spacer of an insulating material having an interior surface and an exterior surface of a spacer bottom shaped to conform to the shape of the first electrical component case major side and a spacer rim shaped to conform with the bend in the perimeter of the first electrical component case major side of the second electrical component;
  applying a pressure sensitive adhesive layer between at least a portion of the interior surface of the further shape conforming insulating spacer and the first electrical component case major side of the second electrical component; and
  applying pressure between the first electrical component case major side of the second electrical component and the shape conforming insulating spacer to adhere the interior surface to first electrical component case major side of the second electrical component.

42. The method of claim 23, further comprising:
  fabricating a further shape conforming insulating spacer of an insulating material having an interior surface and an exterior surface of a spacer bottom shaped to conform to the shape of the first electrical component case major side and a spacer rim shaped to conform with the bend in the perimeter of the first electrical component case major side of the second electrical component;
  applying adhesive in a pattern between a portion or portions of the interior surface of the further shape conforming insulating spacer and the first electrical component case major side of the second electrical component; and
  adhering the interior surface of the shape conforming insulating spacer against the first electrical component case major side of the second electrical component.

43. The method of claim 23, wherein the electrical component sub-assembly comprises first and second capacitors, each capacitor comprising:
  a capacitor case comprising first and second generally opposed, capacitor case major case sides joined together through a continuous capacitor case minor side that maintains the first and second capacitor case major case sides substantially in parallel alignment, whereby the junction of the first capacitor case major side with the capacitor case minor side defines a perimeter having a bend radius;
  an anode and cathode assembly comprising at least one anode, one cathode, a separator interposed between the anode and cathode and electrolyte disposed within the capacitor case; and
  anode and cathode terminals coupled with the respective anode and cathode for making electrical connection with the interconnecting circuitry.

* * * * *